United States Patent

Mastronardi et al.

[11] 4,422,177
[45] Dec. 20, 1983

[54] CT SLICE PROXIMITY ROTARY TABLE AND ELEVATOR FOR EXAMINING LARGE OBJECTS

[75] Inventors: Richard Mastronardi, Medford; Alan DeCew, Newtonville; David McMahon, Malden, all of Mass.

[73] Assignee: American Science and Engineering, Inc., Cambridge, Mass.

[21] Appl. No.: 388,879

[22] Filed: Jun. 16, 1982

[51] Int. Cl.³ .................... A61B 6/04; G01N 23/04; G01N 23/18
[52] U.S. Cl. ........................ 378/17; 378/10; 378/20; 378/208
[58] Field of Search .............. 378/4, 20, 10, 208, 378/209, 17

[56] References Cited

U.S. PATENT DOCUMENTS

| | | | |
|---|---|---|---|
| 3,766,387 | 10/1973 | Heffan et al. | 378/17 |
| 3,867,634 | 2/1975 | Hounsfield | 378/20 |
| 3,973,126 | 8/1976 | Redington | 378/17 |
| 4,316,091 | 2/1982 | Bernardi | 378/17 |

*Primary Examiner*—Eugene La Roche
*Assistant Examiner*—T. N. Grigsby

*Attorney, Agent, or Firm*—Pollock, Vande Sande & Priddy

[57] ABSTRACT

A Computerized Tomography (CT) system for examining large objects, e.g., rocket motors, includes an improved support structure comprising a large bearing and an elongated cup-like support attached to the inner race of the bearing and extending away from the bearing in coaxial relation thereto for supporting the object to be examined and for rotating that object about the axis of the bearing. Spacers or an elevator are provided adjacent the bottom of the cup-like structure for selectively translating the object being examined along the axis of the support structure and bearing. An X-ray source is positioned to beam X-rays through the object being examined at a diametral plane in said object closely adjacent to one face of the bearing, and a detector is also provided which is responsive to X-rays passing through the object to determine the X-ray opacity of a slice of said object closely adjacent to the bearing. The source and detector, or alternatively the bearing and cup-like support, are mounted for translation in a direction transverse to the beam direction. The support structure may be oriented vertically within a pit located below the door of a building structure, with the bearing, source and detector being located above the floor.

14 Claims, 2 Drawing Figures

CT SLICE PROXIMITY ROTARY TABLE AND ELEVATOR FOR EXAMINING LARGE OBJECTS

BACKGROUND OF THE INVENTION

The present invention relates to a Computed Tomography (CT) system for examining large objects such as rocket motors, ingots, pipes, etc., and is more particularly concerned with a novel handling arrangement, comprising a proximity bearing and associated elevator cup, adapted to rotate and elevate the object being examined.

CT systems per se are well known in the art, and comprise a source of radiation and an associated detector arranged to be rotated, or rotated and translated, relative to an object for purposes of examining a sectional slice of the object by means of penetrating radiation. The precision with which the positions of the X-ray source, detector and object are maintained and known is related directly to spatial resolution. The finer these precisions and accuracies are, the better the spatial quality of the final image will be. Accordingly, CT systems used heretofore are normally arranged to predetermine the positions of the X-ray source, detector and object relative to one another, and to maintain those relative positions during examination of the object slice. Such fixing and maintenance of position can be accomplished in a relatively straightforward manner when the object being examined is comparatively small in size, e.g., a portion of the human body.

When the object being examined does not lend itself to being positioned relative to the X-ray source and detector, other techniques must be employed to achieve a final image of acceptable spatial quality. If, for example, there are changes in the position of the axis of rotation of the object being examined and the expected position of that axis relative to the X-ray beam, such changes in position can be taken into account by use of either linear and/or angular monitoring equipment with feedback to the system, or by use of additional software and increased computer time needed to determine the center of rotation for each scan. These techniques increase the cost of the overall system and have limited applicability.

The problems discussed above become almost insurmountable when the object being examined is extremely large or unwieldy. In the case of a rocket motor, for example, which may typically have a length up to 25 feet, a diameter up to seven feet, a weight of 80,000 pounds and which contains a live propellant making it necessary to handle the rocket motor with extreme care, it has been virtually impossible heretofore to support and manipulate the motor with the precision needed for a CT examination thereof. While bearings are presently available which are sufficiently large to rotate a rocket motor of the dimensions specified, if the bearing or a rotary table with which it is associated is located adjacent one end of the rocket motor, e.g., as in the rocket motor inspection system described in Heffan et al U.S. Pat. No. 3,766,387, the normal bearing runout, when magnified by an object which is as tall as a rocket motor, is unacceptable in a CT system.

The present invention is intended to obviate these problems by the provision of a novel handling system adapted to support and manipulate large objects in a fashion permitting examination thereof by known CT techniques.

SUMMARY OF THE INVENTION

The present invention relates to a CT system for large objects, characterized by a supporting structure which incorporates a commercially available bearing, and which is so arranged relative to the radiation source and detector forming a portion of the CT system that every slice of the object being examined is scanned as closely as possible to the bearing plane. This arrangement avoids amplification of bearing radial and axial runout tolerances, reduces to insignificance variations in the axis of rotation of the object being examined at the diametral location in the object at which the slice is being taken, and eliminates the need for special monitoring equipment or software that would have to be employed if there were any significant variation in the position at which the axis of rotation actually is relative to where it is supposed to be in relation to the beam produced by the radiation source.

The support system of the present invention is adapted to rotate and elevate the object being examined by means of a proximity bearing and elevator cup. It includes a large rotary bearing having an inner diameter sufficiently large to encircle the object to be inspected, e.g., a rocket motor, with the object passing through the inner race of the bearing, an elongated cup-like support structure which is attached to the inner race of the bearing for rotation therewith, the support structure extending away from one side of the bearing in substantially coaxial relation to the bearing, and an elevator or spacer structure disposed adjacent the bottom of the cup-like support structure for varying the axial position of the object being examined along the axis rotation of the bearing and of the associated cup-like support structure. An X-ray source is positioned adjacent the rotary table and elevator for beaming X rays (a fan beam or a flying spot pencil beam) through the object to be examined, in a plane which is disposed transverse to the axis of rotation of the bearing and which is positioned closely adjacent to one face of the bearing, whereby the beam passes through the object being examined at a diametral location in the object closely adjacent to said one face of the bearing. The system further includes X-ray detector means which are responsive to X-rays that have passed through the object at the diametral slice of interest, for detecting the X-ray opacity of the object at said diametral slice. The data acquired at the output of the detector is processed in accordance with known CT techniques to produce an image of the slice being examined.

The bearing and associated cup-like support can be oriented and used with the axis of rotation either vertical or horizontal, but will be described hereinafter for purposes of simplicity in reference to a vertical system. In such an arrangement, the X-ray source and detector can be mounted on the floor of a building structure, or on appropriate frames which are in turn mounted on the floor, and the rotary bearing and downwardly depending elevator cup can be disposed between the source and detector with the elevator cup extending below the floor of the building structure into an underlying pit.

The object being examined, e.g., a rocket motor, is variably displaced along the axis of rotation of the bearing and support structure by means of differently dimensioned spacers that are inserted between the bottom of the elevator cup and the bottom of the object being examined, or by use of a hydraulic or electro-mechanical elevator located below the bottom of the object being examined, thereby to select, and vary as needed, the diametral location at which the CT slice is to be taken; and the object being examined is rotated in the course of data acquisition by rotating the bearing and the elevator cup which supports the object. Inasmuch as the diameter of the object being examined is considerably larger than the included angle of the fan beam or flying spot X-ray source employed, the object being examined must also be translated in a direction transverse to the direction of the X-ray beam to acquire complete data for each slice. Such translation can be accomplished by either moving the source and detectors laterally relative to the bearing and its associated elevator cup, or by moving the bearing and cup laterally while the source and detectors remain stationary.

Each of the foregoing arrangements is characterized by the proximity of the bearing to the object slice being examined, and by the fact that the elevator is rigidly set with respect to the bearing and does not move relative to the bearing during the data acquisition sequence. This produces a number of advantages, i.e., where precise alignment of the source and detectors is required, because of collimation, etc., the source and detectors can be left stationary with all motion taking place on the object being examined. Moreover, by having the bearing as close to the X-ray slice as possible, amplification of bearing radial and axial runout tolerances is avoided, and the object center of rotation is precisely maintained relative to the source and detector, thereby achieving high resolution. Further, elevation precision laterally and angularly is no longer a driver on the system precision, and the CT image is accordingly rendered insensitive to the elevator precision, a result which has been most difficult to obtain on existing large object rotary tables and elevators.

BRIEF DESCRIPTION OF THE DRAWINGS

The foregoing objects, advantages, construction and operation of the present invention will become more readily apparent from the following description and accompanying drawings, wherein.

DESCRIPTION OF THE PREFERRED EMBODIMENTS

The present invention permits the application of known CT techniques to the examination of extremely large objects. It will be described hereinafter in reference to the examination of a rocket motor, whose dimensions can be as large as seven feet in diameter and 25 feet in length, and with reference to the examination of such a rocket motor by means of a vertically oriented support system which extends into a pit located below the floor of a building structure in which the overall system is housed. As will be apparent to those skilled in the art, the system can also be used for the examination of other types of large objects, and can be used in a horizontal rather than in a vertical orientation. When used in a vertical orientation with a pit, the examination procedure will depend in part upon the facility in which the pit is provided and, more particularly, on the depth of the pit. If the pit is sufficiently deep, and contains a downwardly depending cup-like support structure of sufficient length, the object being examined can be completely examined in the course of a single pass of the object upwardly along the axis of rotation of the elevator cup and its associated bearing. This is the preferable procedure when a rocket motor is being handled inasmuch as the rocket motor contains live propellant, and it is desirable to handle the motor as little as possible. However, if the pit and downwardly depending cup structure are not deep enough to permit such examination in a single pass, the motor can be examined at various slice locations along a portion of its axial length, and then turned through 180° and reinserted into the support structure to permit examination of the remaining portion of its axial length.

In the case of a rocket motor, the examination by the CT equipment of the present invention is intended to detect flaws of the type referred to in Heffan et al U.S. Pat. No. 3,766,387, and is capable of determining the presence and location of cracks down to a width of 0.003 inches or 0.004 inches in the propellant, or a debond or delamination in the casing, or between the casing and propellant, or in any of the several layers of the overall motor structure. In addition, the invention is operative to detect areas in the propellant where there is a variation in density as low as two centimeters in diameter or spherical, and as little as a 2% difference in the density of the background material.

Figure 1:
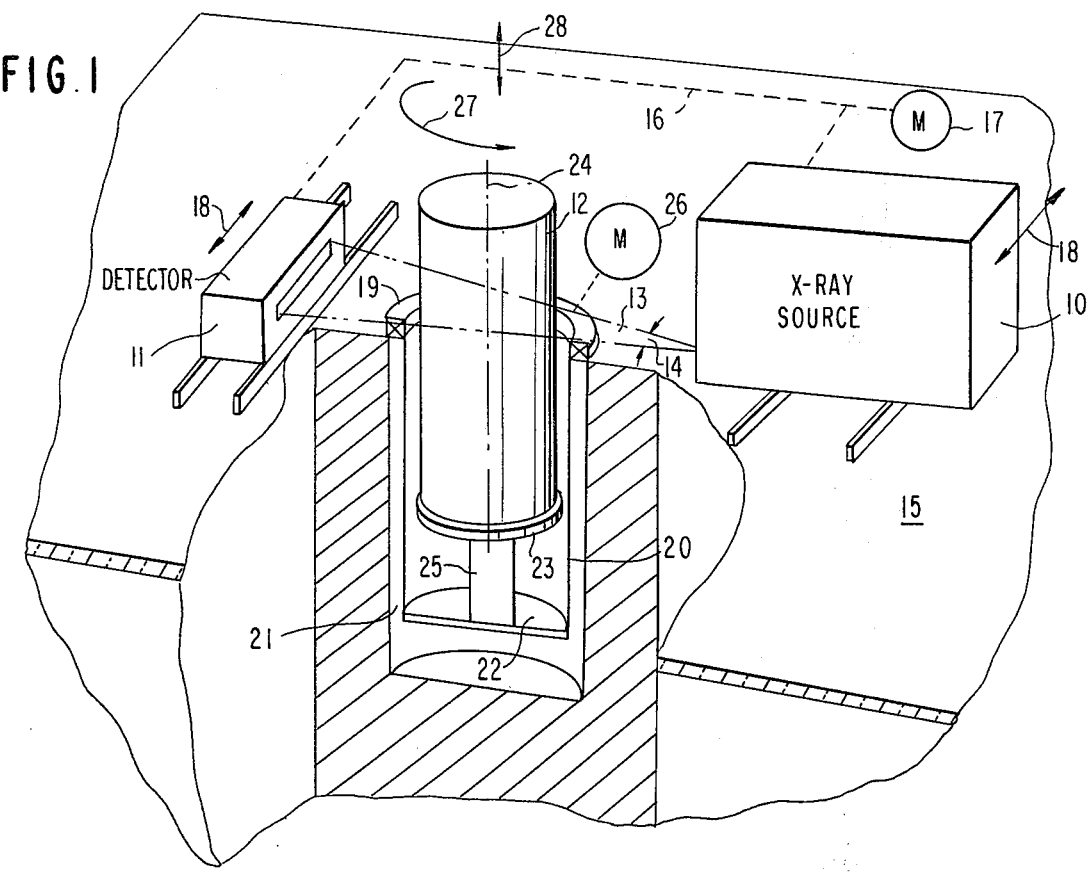
FIG. 1 illustrates a system constructed in accordance with one embodiment of the present invention.

As shown in FIG. 1, the system includes an X-ray or radiant energy source 10 and an associated detector 11 which are located in spaced relation to one another on opposite sides of an object 12, e.g., a rocket motor, to be examined. The source 10 must provide energy which is sufficiently high to penetrate the six feet to seven feet diameter of the rocket motor 12, i.e., the system of the present invention is a high energy CT system. The source can be a so-called Linatron, which is commercially available from Varian Associates, Inc., Palo Alto, Calif., and which is adapted to produce high energy X-rays, e.g., 15 mev. but radiation sources of other types can be employed. The source beams radiant energy through a diametral slice of rocket motor 12, as indicated at 13, in a fan beam which has an included angle 14. In the alternative, however, the source employed can provide radiation in the form of a pencil beam of energy which is scanned through the angle 14. In either case, energy which passes through the rocket motor 12 is detected by detector 11 to provide output data representative of the radiation opacity of motor 12. As the rocket motor 12 is translated relative to source 10, and as the rocket motor is rotated about its central axis, successive sets of data are acquired which are processed in known fashion by a computer and used to generate a display of the rocket slice or diametral cross section of interest.

For purposes of stability, source 10 and detector 11 can be mounted on or closely adjacent to the floor 15 of a building structure, or on a stable frame which is in turn mounted on the floor 15. In the particular embodiment shown in FIG. 1, source 10 and detector 11 are mechanically connected to one another as at 16 so that they may be moved in translation by a motor 17 in the directions of arrows 18, i.e., in a direction transverse to the direction of beam 13. As noted earlier, inasmuch as the included angle 14 of beam 13 is less than the full diameter of the rocket motor 12, such relative translation is required to obtain all data for image reconstruction.

A large bearing 19, whose inner diameter is sufficiently large to encircle rocket motor 12, is mounted in fixed position on or closely adjacent to floor 15 between source 10 and detector 11. As illustrated in FIG. 1, an important characteristic of all of the embodiments of the present invention is the location of bearing 19 relative to source 10 and detector 11, i.e., the relative location of these components is such that beam 13 always passes through rocket motor 12 at a diametral location or slice of said motor directly adjacent to one face of bearing 19. For reasons mentioned previously, and as will be apparent as this description proceeds, this location of the radiant energy beam relative to the bearing is needed to assure that the spatial resolution of the final image is not degraded by axial or radial movement of the portion of motor 12 at which the slice is being taken.

An elongated cylindrical support structure 20 is attached to the inner race of bearing 19 and extends downwardly from the bearing, in coaxial relation thereto, into a cylindrical pit 21 that is located below floor 15. Support structure 20 is of cup-like configuration, has an open top adjacent bearing 19, and a closed bottom 22, and has been depicted in FIG. 1 as having a continuous side wall. Variations in this configuration are possible, however, i.e., the cup-like support 20 can have a discontinuous side wall, or can be defined by a number of downwardly depending, spaced structural beams, rods or the like.

A support table 23 is located within cup-like structure 20 for supporting rocket motor 12 thereon, and said table 23 can be variably displaced relative to the bottom 22 of the structure 20, along the central axis 24 of the bearing 19 and support 20, by means of an intervening structure generally designated 25. Structure 25 can take the form of replaceable, differently dimensioned spacers, or in the alternative, can comprise an appropriate hydraulic or electro-mechanical motor-driven elevator. In either case, the cup 20 is deeper than one-half the length of motor 12, so that cup 20 provides lateral support for motor 12 even with the highest spacer in place. The structure 25 employed is such that the axial positioning of the motor 12 is rigidly set with respect to bearing 19, and does not move with respect to the bearing, during the data acquisition sequence.

A motor 26 and associated gear train are coupled to bearing 19 to rotate said bearing, as well as cup 20, table 23, and rocket motor 12 supported thereby, about axis 24 as indicated by arrow 27. Such rotation of the object 12, and associated relative translation of the source 10 and detector 11, are in themselves known in other CT systems of the so-called second generation type, and are employed to permit the acquisition of data at the slice location of interest, immediately adjacent to the upper surface of bearing 19. When data acquisition has been completed at the slice of interest, the rocket motor 12 is displaced longitudinally along axis 24, as indicated by arrow 28, by means of spacers or elevator 25, whereafter data may be acquired with respect to the new slice which is then intercepted by X-ray beam 13.

More particularly, the angle 14 of beam 13 is typically 20°, and the beam 13 accordingly intercepts only a limited portion of the diametral plane of rocket motor 12 at any given position of source 10 relative to rocket motor 12. In practice, therefore, for each angular position of rocket motor 12, data is first acquired by moving source 10 and detector 11 in direction 18 until the beam 13 has passed transversely through the entire diametral plane of interest. Motor 26 then rotates support structure and rocket motor 12 through a 20° angle; the source and detector arrangement 10, 11 are then moved in the reverse direction 18 until beam 13 again passes through all portions of the diametral plane of interest; support 20 and rocket motor 12 are then again indexed through a further 20° angle, etc. The data acquired at the output of detector 11 during each traverse of source 10 and detector 11, for each angular position of rocket motor 12, is stored, processed, and used to produce a visual image by known techniques. Thereafter, the rocket motor 12 is moved axially, i.e., in direction 28, through an appropriate increment by changing the size of the spacer or operating the elevator which comprise means 25, thereby to cause beam 13 to pass through a different slice of rocket motor 12, whereafter the same translation and incremental rotation steps are effected to acquire data relating to the new slice. This procedure is continued until the rocket motor has been completely inspected.

Figure 2:
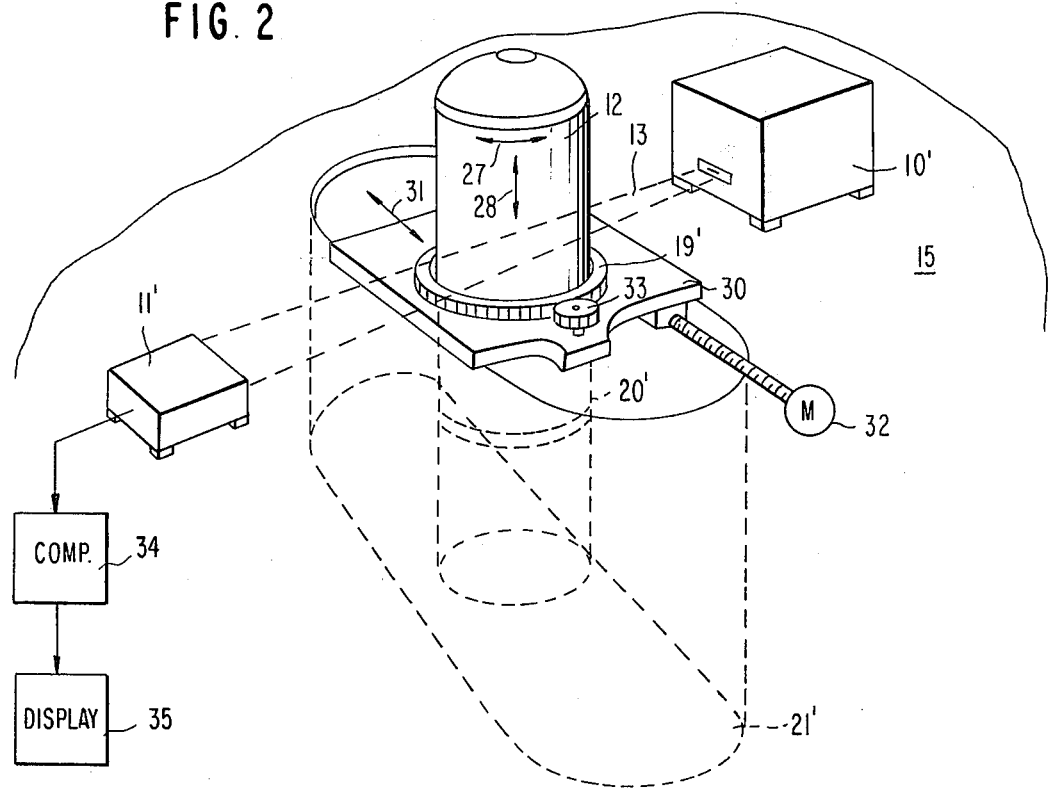
FIG. 2 illustrates a second embodiment of the invention.

The alternative arrangement shown in FIG. 2 is generally similar to that described in reference to FIG. 1 except that X-ray source 10' and detector 11' are now mounted in fixed position on floor 15 (or on an associated frame attached to the floor), and bearing 19' and its associated cup-like support 20' are mounted on a frame 30 which is adapted to be moved in translation in a direction 31, transverse to beam 13, by means of a motor 32. To accommodate this translational movement of bearing 19' and the underlying support structure, as well as of rocket motor 12 carried thereby, the pit 21' is now of elongated cross section. As in the case of FIG. 1, the support structure and rocket are adapted to be rotated by an appropriate motor and gear, depicted at 33 in Fig. 2. The output of detector 11' is supplied, as before, to a computer and associated display, generally depicted in Fig. 2 at 34 and 35.

While we have thus described preferred embodiments of the present invention, many variations will be apparent to those skilled in the art. It must therefore be understood that the foregoing description is intended to be illustrative only and not limitative of the present invention and all such variations and modifications as are in accord with the principles described are meant to fall within the scope of the appended claims.

Having thus described our invention, we claim:

1. A Computerized Tomography system for inspecting large objects, comprising a rotary bearing having an inner diameter sufficiently large to encircle the object to be inspected, an elongated cup-like support structure attached to said bearing for rotation therewith, said support structure extending away from one face of said bearing in coaxial relation to said bearing, said support structure being adapted to receive and support an object to be examined with said object protruding outwardly of said support structure through said bearing and past the other face of said bearing, drive means coupled to said bearing for rotating said bearing, said support structure, and the object to be examined about the central axis of said bearing and support structure, a radiant energy source positioned to beam radiant energy toward the object to be examined in a direction transverse to the axis of rotation of said bearing, said beam passing through a diametral plane in said object closely adjacent to said bearing, detector means positioned adjacent said object for detecting the radiant energy opacity of said object at said dimetral plane thereof, and translation means for selectively displacing said object along the axis of said support structure and through said bearing, to change the diametral plane of the object being examined without changing the position of the diametral plane under examination relative to said bearing.

2. The system of claim 1 wherein said cup-like support structure includes a bottom which is disposed transverse to said axis of rotation at a position remote from said bearing, said translation means comprising spacers disposed between said bottom of said support structure and the object to be examined.

3. The system of claim 1 wherein said cup-like support structure includes a bottom which is disposed transverse to said axis of rotation at a position remote from said bearing, said translation means comprising motor-driven elevator means disposed between said bottom of said support structure and the object to be examined.

4. The system of claim 1 wherein said source and detector means are located in horizontally spaced relation to one another, said bearing and support structure being disposed between said source and detector means and with their said central axis oriented vertically.

5. The system of claim 4 including a building structure for housing said system, said support structure extending at least partially below the floor of said building structure into a pit provided below said floor.

6. The system of claim 5 wherein said pit has a circular cross section.

7. The system of claim 5 wherein said pit has an elongated cross section.

8. The system of claim 1 wherein said bearing, said source, and said detector means are each located above the floor of a building structure, said support structure extending downwardly from said bearing into a pit provided below the floor of said building structure.

9. The system of claim 8 wherein said source and detector means are fixed in position relative to the floor of said building structure at locations closely adjacent said floor.

10. The system of claim 1 or claim 8 including means for moving said source and said detector means together in a direction transverse to the central axis of said bearing and support structure and transverse to the beam direction of said radiant energy beam.

11. The system of claim 1 or claim 8 including means for moving said bearing and support structure together in a direction transverse to the central axis thereof.

12. The system of claim 1 wherein said diametral location in said object is closely adjacent to said other face of said bearing.

13. The system of claim 1 wherein said source is operative to produce a fan beam of X-rays.

14. The system of claim 1 wherein said source is operative to produce a pencil beam of X-rays which is scanned as a flying spot across at least a portion of a slice of the object to be examined.

* * * * *